United States Patent [19]

Boucly

[11] Patent Number: 5,607,408
[45] Date of Patent: Mar. 4, 1997

[54] APPLICATION OF ACTIVE SKIN TREATMENTS UNDER NEUTRAL ATMOSPHERE

[76] Inventor: Yvonne Boucly, 24, Rue Du Mont Valérien, 92210-Saint Cloud, France

[21] Appl. No.: 353,065

[22] Filed: Dec. 9, 1994

[51] Int. Cl.$^6$ .................................................. A61M 35/00
[52] U.S. Cl. ........................... 604/289; 604/303; 604/23; 128/202.17; 128/206.21
[58] Field of Search .................. 604/23, 24, 289, 604/303, 290, 292–294; 128/898, 202.13, 202.17, 206.21, 202.25, 202.16

[56] References Cited

U.S. PATENT DOCUMENTS

| | | | |
|---|---|---|---|
| 2,138,428 | 11/1938 | Pulgar | 604/303 X |
| 2,655,145 | 10/1953 | Heger . | |
| 3,088,459 | 5/1963 | Rabinoff | 604/303 X |
| 3,345,987 | 10/1967 | Ediin | 604/23 X |
| 3,587,577 | 6/1971 | Smirnov et al. | 604/23 X |
| 3,908,655 | 9/1975 | Lund | 604/23 X |
| 4,151,843 | 5/1979 | Brekke et al. | 128/205.25 X |
| 4,182,329 | 1/1980 | Smit et al. | 604/23 X |
| 4,474,571 | 10/1984 | Lasley | 604/23 |
| 4,801,291 | 1/1989 | Loori | 604/23 |
| 5,029,579 | 7/1991 | Trammell | 128/206.26 |
| 5,154,697 | 10/1992 | Loori | 604/23 |
| 5,400,781 | 3/1995 | Davenport | 128/205.25 X |
| 5,429,123 | 7/1995 | Shaffer et al. | 128/205.25 X |
| 5,447,504 | 9/1995 | Baker et al. | 604/289 |
| 5,474,060 | 12/1995 | Evans | 128/205.25 X |

FOREIGN PATENT DOCUMENTS

| | | |
|---|---|---|
| 1346990 | 11/1963 | France . |
| 2240715 | 3/1975 | France . |

*Primary Examiner*—Randall L. Green
*Assistant Examiner*—Chalin Smith
*Attorney, Agent, or Firm*—Kenneth P. Robinson

[57] ABSTRACT

Skin treatment solutions are applied to the face, for example, by use of a flexible opaque mask 10. On a timed basis, one or more treatment solutions from vials 24–26 are provided to various facial areas via flexible tubes 20. In order to enable use of active treatment solutions including vitamin formulations subject to oxidation degradation in the presence of air, for example, a neutral atmosphere is provided. This is accomplished by supplying a neutral gas, such as nitrogen, from a cylinder 50 to mask 10 via flexible tubes 48. The neutral gas is infused between the mask 10 and the underlying skin at a low over pressure sufficient to drive air out from under the mask. Single treatment quantities of treatment solutions can be intermittently applied on a timed basis by the action of pump 36 operating under the control of programmable timers 30 and 40.

20 Claims, 1 Drawing Sheet

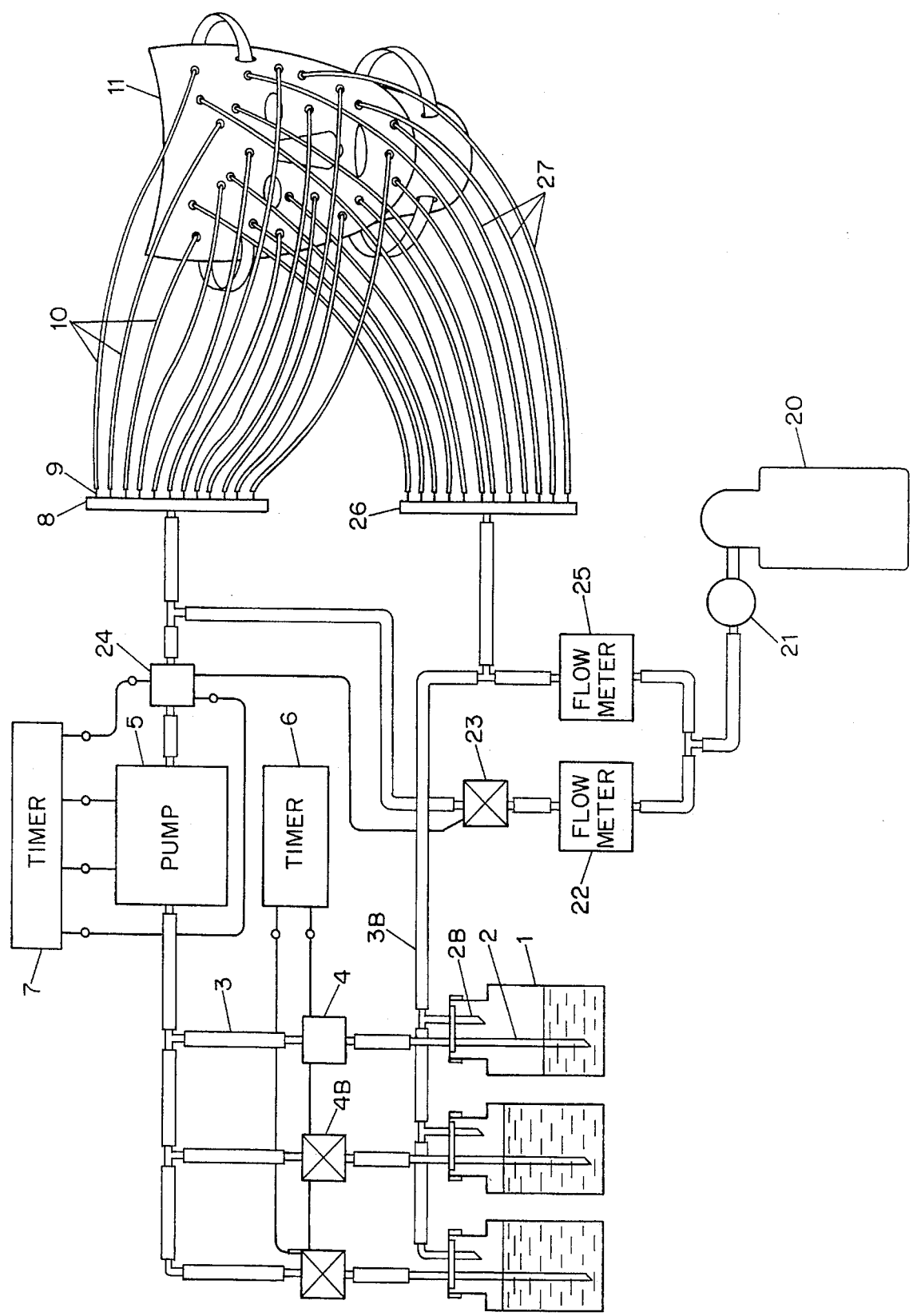

APPLICATION OF ACTIVE SKIN TREATMENTS UNDER NEUTRAL ATMOSPHERE

The invention relates to the application of skin treatments and, more particularly to the application of active treatments, containing ingredients such as forms of vitamins A, C and E, under a neutral atmosphere, such as nitrogen.

BACKGROUND OF THE INVENTION

Many facial and other skin treatments utilize treatment solutions, such as creams or lotions, which contain forms of vitamins A, C or E or other active substances. Typically, these active substances are subject to degradation by oxidation or other effects when exposed to air or components of light such as ultra violet (UV) radiation. Thus, certain pharmacopeia, such as the American Pharmacopeia, XXIst edition, pages 1118 and 1215, recommend that preparations containing vitamins such as A, C or E be stored and handled so as to be shielded from light and from atmospheric oxygen by an atmosphere of a neutral or inert gas.

However, in prior skin treatment usage these types of treatment solutions have been applied to the skin in a manner not providing adequate protection from exposure to light or air, or both. No suitable arrangements enabling active skin treatments to be applied in a practical manner, while at the same time providing protection from exposure to both air and light, are known to have been previously available.

It is therefore an object of this invention to provide apparatus and methods for applying skin treatments which are characterized by one or more of the following:

protection from exposure to air;

protection from exposure to light;

automated application of facial treatments under a mask;

infusion of nitrogen under a masking device to impede air contact with active treatment solutions; and use of a masking device arranged to constrain transmission of light and enable infusion of both treatment solutions and a neutral gas under the masking device.

BRIEF SUMMARY OF THE INVENTION

In accordance with the invention, apparatus for applying skin treatment solutions in the presence of a neutral gas includes masking means including a plurality of openings and configured for placement over an area of skin. A first fluid circuit is arranged to provide at least one treatment solution to the area of skin via a first opening arrangement comprising a plurality of the openings in the masking means. A second fluid circuit is arranged to provide a neutral gas via a second opening arrangement comprising at least one of the openings in the masking means, The masking means may take the form of a flexible mask arranged to at least partially constrain both the escape of gas infused between the mask and an area of facial skin of an individual and the transmission of UV radiation. The openings of the first opening arrangement are configured to enable a treatment solution to be dispensed onto the area of skin and each opening of the second opening arrangement is configured to enable a gas such as nitrogen to be infused between the masking means and the area of skin.

Also in accordance with the invention, a method for dispensing skin treatment solutions in the presence of a neutral gas, comprises the steps of:

(a) placing a masking device having a plurality of openings over a skin area;

(b) providing a treatment solution to the skin area via a first opening arrangement comprising a plurality of openings in the masking device; and (c) infusing a neutral gas between the enclosure device and the skin area via a second opening arrangement comprising at least one of the openings in the masking device.

For a better understanding of the invention, together with other and further objects, reference is made to the accompanying drawings and the scope of the invention will be pointed out in the accompanying claims.

BRIEF DESCRIPTION OF THE DRAWING

The drawing shows an embodiment of the invention including a facial mask enabling application of active treatment solutions in a nitrogen gas atmosphere.

DESCRIPTION OF THE INVENTION

In the illustrated embodiment, apparatus for applying skin treatment solutions in the presence of a neutral gas includes masking means, shown as facial mask 10. The masking means 10 is configured for placement over an area of skin which may be the skin of the face or other body portion. In the latter case the masking device would be dimensioned in a form suitable for placement over the other body portion, so that the masking device may have a form other than the facial mask shown. As shown, mask 10 includes a plurality of openings including an opening indicated at 12 which is representative of a first opening arrangement and an opening indicated at 14 which is representative of a second opening arrangement. Mask 10 may be constructed of flexible opaque plastic or other suitable material and may include fastening devices such as straps 11.

The illustrated apparatus also includes a first fluid circuit, shown as liquid circuit 16, arranged to provide at least one treatment solution to the area of skin via the first opening arrangement represented by opening 12. The liquid circuit 16 includes dispatcher means 18 for distributing a treatment solution to a plurality of outputs shown connected to opaque flexible tubes 20. As shown, each of the twelve flexible tubes 20 connects to an individual opening, such as 12, of a first opening arrangement comprising a plurality of the openings in the mask 10. In a currently preferred embodiment there are included twenty of the flexible tubes 20, twelve tubes being shown in the drawing for purposes of illustration only. Liquid circuit 16 also includes at least one treatment solution input tube 22 arranged for coupling to a vessel containing a treatment solution. Three such vessels, which may be opaque vials, are shown at 24, 25 and 26. As shown, input tubes 22 extend through closure caps 28 into the treatment solutions within the vials 24–26.

Liquid circuit 16 further includes flow means for causing treatment solution to flow into one or more of input tubes 22 for coupling to the dispatcher means 18. As illustrated, the flow means includes a programmable timer 30 controlling solenoid valve 32 and normally-closed solenoid valves 33 and 34, which are arranged to permit or prevent the flow of treatment solutions out of the vials 24–26. Pump 36 and solenoid valve 38, operating under the control of programmable timer 40, are arranged to draw predetermined portions of treatment solutions from the vials 24–26 for coupling to the dispatcher 18 via an arrangement of opaque coupling tubing (which may include interconnecting sections and Ts as shown) indicated collectively at 42.

The illustrated apparatus further includes a second fluid circuit, shown as gas circuit 44, arranged to provide a neutral gas via the second opening arrangement represented by opening 14 in the masking device 10. Since a gas such as nitrogen may be readily infused between the mask and the surface of the skin under the mask, in other arrangements the second opening arrangement may consist of only one or a few openings, rather than the total of twelve openings shown coupled to dispatcher 46 via flexible tubes 48, as will be further described.

Gas circuit 44 as shown is coupled to a vessel, illustrated as gas cylinder or tank 50 containing a neutral gas, such as nitrogen, under pressure. Nitrogen is typically provided at 3,000 pounds per square inch (psi) within cylinder 50 and reduced to about 40 psi by action of gas regulator 52. Flowmeter 54 controls the flow of nitrogen to the dispatcher 46 and thereby to the mask 10, via flexible tubes 48. As shown, the gas is coupled via an arrangement of coupling tubing (which may include interconnecting sections and Ts as shown) indicated collectively at 60. As shown, tubing arrangement 60 also provides nitrogen, via gas supply tubes 62, to the vials 24–26 to compensate for decreasing levels of treatment solutions and, via flow meter 56 and normally-closed solenoid valve 58, to tubing arrangement 42 (via T 64) for use in clearing treatment solutions from dispatcher 18 and flexible tubes 20. As will be appreciated, in particular applications, persons skilled in the art can provide suitable arrangements for manual setting and control of the various elements of the liquid and gas circuits 16 and 44 or for overall control by use of an appropriately programmed microprocessor (not shown), once the invention and its operation are understood. Also, in other embodiments it may be desirable to omit pump 36 and arrange to utilize the pressurized gas from cylinder 50, supplied via tubes 62, to drive the treatment solutions from the vials 24–26 under the control of a suitable arrangement of controlled valves.

Specific features of the apparatus and its operation in the illustrated embodiment will now be considered in somewhat greater detail. The apparatus is composed of a liquid fluid circuit 16, and a neutral gas fluid circuit 44. Both fluids contact each other under a masking device, such as flexible mask 10, maintained over the face or, as the case may be, over a selected body portion. All of the components and associated mechanisms can be accommodated within a metal or plastic housing (not shown), an external side of which is used as a control panel.

The liquid fluid circuit 16 is arranged for access to the treatment solutions which have previously been packaged into opaque vials 24–26 under a neutral atmosphere and are successively placed vertically in the apparatus. By means of a bevel cut stainless steel input tube 22, having a small diameter and a length at least equal to the vial height, a rubber plug provided with an aluminum crimp cap 28 may be perforated, and the tube 22 inserted down close to the vial bottom. The stainless steel input tubes 22 are connected, via opaque tubing arrangement 42, to a low flow-rate metering or peristaltic pump 36 with a flow rate of a few milliliters per minute. Between the vial outlet and the pump, a solenoid valve 32 driven by programmable timer 30 regulates the vial samplings. The pressure drop caused within the vials by pumping the liquid is compensated for by supplying neutral gas from gas fluid circuit 44 to the gas supply tubes 62. According to the treatment duration, one or more of the products contained in the vials are thus sampled alternately and intermittently. The idle period between two dispensings as well as the volumes of samples in each vial are determined before each treatment. The data (times and volumes) are recorded within the programmable timers 30 and 40, which drive the solenoid valves 32–34 mounted downstream from the vials and the metering pump 36, respectively.

During the active phase, the solution pumped from the vials will be directed to the dispenser-dispatcher 18. The dispatcher 18 may be a device of circular or rectangular shape, the entry side of which is provided with a single hole in which a 1–2 cm. long tube has been welded. To this tube is attached a flexible tube coupled to the metering pump 36. Dispatcher 18 thus functions as a small container in which the treatment solution entering through a single hole on one side, exits through a large number of holes in the manner of a sprinkling rose. In each exit hole is welded a small metal tube having a length of about one centimeter and a small diameter, to which a section 20 of opaque plastic flexible tubing is connected, which in turn connects the dispatcher 18 to the mask 10. The tubes 20 may be attached to the mask 10 by means of small plastic rigid tubes thermally welded to the mask wall. Each of these tubes 20 is thereby arranged to open at a selected location in the areas to be treated: forehead, cheeks, neck, etc.

In the idle phase, that is, when the pump 36 is stopped, the treatment solution retained in the tubing 20 connecting the dispatcher to the mask, is nevertheless desirably diffused over the skin. This diffusion step is carried out by means of the neutral gas sampled downstream from the pressure-reducing valve 52 into the gas fluid circuit 44 described above. At the outlet of the gas pressure-reducing valve 52, the gas circuit is divided into two branches. In one of them, the amount of neutral gas required for propelling the liquid treatment solution to the mask is sampled, and a solenoid valve 58 normally closed when idle is energized by the programmable timer 40 when the pumping cycle ends. The propeller gas thus released has its flow-rate and pressure regulated by means of a flow meter 56. A solenoid valve 38 whose open/close cycle is inverted relative to that of solenoid valve 58, lets the treatment solution pass through, and then closes the circuit during the time when the metering pump 36 is stopped. The propeller gas released by the solenoid valve 58 pushes the treatment solution beyond the dispatcher 18 all the way to the mask 10.

The gas fluid circuit 44, utilizes compressed nitrogen as a neutral gas source. The gas may be contained in a non-reloadable cartridge or in a reloadable cylinder. The reloadable cylinder 50 which is more economical and has a capacity adapted to the size of the apparatus, is currently preferred. The cylinder is equipped with a pressure regulator 52 comprising a downstream pre-set pressure-reducing valve. At the outlet of the pressure-reducing valve, the circuit is divided into two branches. On one of those branches, the gas is used to propel the treatment solution via dispatcher 18 as described above, and on the other branch, by means of a flow meter 54, the amount of gas necessary for the treatment is sampled. The gas is then diffused over the skin by means of a dispatcher 46 which may be identical to the one used for diffusing the treatment solution. The dispatcher 46 is also connected to the mask 10 by means of a sufficient number of flexible opaque tubes 48 to ensure a proper flow of the neutral gas under the mask so as to cause a small over-pressure, which prevents ambient air from entering. As discussed, based on the effectiveness of the infusion of gas under a particular masking device and the fit and other characteristics of the masking device itself, only one or a few of flexible tubes 48 may be required for effective operation. In such cases, dispatcher 46 may be unnecessary or may be replaced by a simpler Y or other junction device.

In application of the invention, a method for dispensing skin treatment solutions in the presence of a neutral gas, comprises the steps of:

(a) placing a masking device 10 having a plurality of openings 12, 14 over a skin area such as the face;

(b) providing one or more treatment solutions to the skin area via a first opening arrangement comprising a plurality of openings 12 in the masking device by activation of liquid circuit 16; and (c) infusing a neutral gas between the enclosure device and the skin area via a second opening arrangement comprising at least one of the openings 14 in the masking device by activation of gas circuit 44, as described.

In use of the method, step (c) is desirably implemented before and during step (b) in order to drive air from between the mask and the skin area before and while the treatment is provided to the skin area. Accordingly, in step (c) nitrogen gas provided under pressure is infused at a reduced pressure level still providing a low over pressure, relative to the prevailing atmospheric pressure. In a currently preferred use of the invention the masking device is an opaque flexible plastic or rubberized mask suitable for covering a facial area and at least partially constraining the escape of the infused nitrogen atmosphere from the space between the mask and the facial area. Types of treatments presently contemplated include facial beauty treatments using solutions containing forms of one or more of vitamins A, C and E, or other active formulations. Particular formulations for use with the invention can be selected by skilled persons and administered under a non-reactive atmosphere of nitrogen or other suitable gas or gas mixture.

While there have been described the currently preferred embodiments of the invention, those skilled in the art will recognize that other and further modifications may be made without departing from the invention and it is intended to claim all modifications and variations as fall within the scope of the invention.

What is claimed is:

1. Apparatus for applying skin treatment solutions in the presence of a neutral gas, comprising:

masking means including a plurality of openings and configured for placement over an area of skin;

a first fluid supply circuit arranged to provide at least one treatment solution to said area of skin via a first opening arrangement comprising a plurality of said openings in the masking means; and a second fluid supply circuit arranged to provide to said masking means a neutral gas via a second opening arrangement comprising at least one of said openings in the masking means.

2. Apparatus as in claim 1, wherein openings of said first opening arrangement are configured to enable a treatment solution to be dispensed onto said area of skin and each opening of said second opening arrangement is configured to enable a gas to be infused between said masking means and said area of skin.

3. Apparatus as in claim 2, wherein said masking means comprises a flexible mask arranged to at least partially constrain both the escape of said neutral gas when infused between said mask and an area of facial skin of an individual and the transmission of UV radiation.

4. Apparatus as in claim 1, wherein said first fluid supply circuit additionally includes a vessel containing a treatment solution containing one of the following: a form of vitamin A, a form of vitamin C, a form of vitamin E.

5. Apparatus as in claim 1, wherein said second fluid supply circuit additionally includes a container of nitrogen gas and is arranged to infuse nitrogen gas between the masking means and the area of skin at a pressure adequate to impede the entry of air between the masking enclosure means and said area of skin.

6. Apparatus as in claim 1, wherein said first fluid supply circuit is arranged to be coupled to at least one vessel, each said vessel containing a quantity of treatment solution adequate for one skin treatment.

7. Apparatus as in claim 6, wherein each said vessel is an opaque vial with a top closure pierced by a tube inserted into said treatment solution and coupled to a pumping arrangement effective to provide quantities of said treatment solution to each opening of said first opening arrangement.

8. Apparatus for applying skin treatment solutions in the presence of a neutral gas, comprising:

masking means including a plurality of openings and configured for placement over an area of skin;

a first fluid circuit arranged to provide at least one treatment solution to said area of skin via a first opening arrangement comprising a plurality of said openings in the masking means; and a second fluid circuit arranged to provide a neutral gas via a second opening arrangement comprising at least one of said openings in the masking means;

said first fluid circuit arranged to be coupled to at least one vessel characterized as follows:

each said vessel is an opaque vial with a top closure pierced by a tube inserted into the treatment solution and coupled to a pumping arrangement effective to provide quantities of said treatment solution to each opening of said first opening arrangement; and each said vessel is arranged with an input tube which couples treatment solution pumped from said opaque vial to a first dispatcher device effective to distribute said treatment solution to a plurality of flexible tubes connected to each opening of said first opening arrangement.

9. Apparatus as in claim 8, wherein a gas tube arrangement carries nitrogen gas to a second dispatcher device effective to distribute said nitrogen gas to a flexible tube connected to each opening of said second opening arrangement.

10. Apparatus for applying skin treatment solutions in the presence of a neutral gas, comprising:

a flexible masking device including a plurality of openings and configured for placement over a skin area;

at least one treatment solution input tube arranged for coupling to a vessel containing a treatment solution;

flow means for causing said treatment solution to flow into said input tube from said vessel containing a treatment solution;

dispatcher means coupled to said input tube for distributing said treatment solution to a plurality of outputs;

a plurality of flexible tubes connecting between said outputs and individual openings of a first opening arrangement comprising a plurality of said openings in the masking device for providing treatment solution to said skin area; and a gas circuit arranged to enable coupling to a gas vessel containing a neutral gas under pressure, said gas circuit including flexible tubing connecting to a second opening arrangement, comprising at least one of said openings in said masking device, for infusing said neutral gas between said masking device and said skin area.

11. Apparatus as in claim 10, additionally including a treatment solution vessel in the form of an opaque vial containing a quantity of a treatment solution adequate for one treatment, coupled to said input tube.

12. Apparatus as in claim 11, additionally including a gas vessel containing nitrogen gas under pressure and arranged for coupling to said gas circuit.

13. Apparatus as in claim 11, in which said opaque vial containing a treatment solution is coupled via said input tube to a solenoid valve controlled by a programmable timer which determines the duration of time periods in which treatment solution is drawn from said opaque vial, and wherein a decreasing level of treatment solution in said opaque vial is compensated by introduction of neutral gas from said gas circuit via a gas supply tube.

14. Apparatus as in claim 10, wherein said flow means includes a pump arranged to cause treatment solution to flow to said dispatcher which comprises a hollow housing having one side with a single entry opening and another side with a plurality of openings to which said plurality of flexible tubes are coupled.

15. Apparatus as in claim 12, wherein said gas circuit includes a pressure reducing valve for controlling release of gas from said gas vessel, a flow meter for regulating gas flow rate to release the amount of gas required for an appropriate gas flow under the flexible mask, and dispatcher means for providing said gas flow to flexible tubing connecting to said at least one of said openings, for infusing gas between the masking device and said skin area.

16. A method for dispensing skin treatment solutions in the presence of a neutral gas, comprising the steps of:

(a) placing a masking device having a plurality of openings over a skin area;

(b) providing a treatment solution to said skin area via a first opening arrangement comprising a plurality of said openings in said masking device; and (c) infusing a neutral gas between said enclosure device and said skin area via a second opening arrangement comprising at least one of said openings in said masking device.

17. A method as in claim 16, wherein step (c) is implemented before and during step (b), in order to drive air from between said masking device and said skin area, before and while said treatment solution is provided to the skin area.

18. A method as in claim 16, wherein in step (c) said neutral gas is nitrogen gas which is provided under pressure and is infused at low over pressure between the enclosure device and the skin area.

19. A method as in claim 16, wherein said masking device is a flexible mask suitable for covering a facial area and at least partially constraining the escape of gas infused between the mask and the facial area.

20. A method as in claim 16, wherein in step (b) at least one treatment solution containing at least one of the following is provided to said skin area: a form of vitamin A, a form of Vitamin C, a form of vitamin E.

* * * * *